United States Patent
Yamamoto et al.

[11] Patent Number: 6,108,030
[45] Date of Patent: Aug. 22, 2000

[54] APPEARANCE INSPECTING DEVICE FOR SOLID FORMULATION

[75] Inventors: Taizo Yamamoto, Osaka; Motohiro Yagyu, Yamabe-gun, both of Japan

[73] Assignee: Japan Elanco Co., Ltd., Nara-ken, Japan

[21] Appl. No.: 09/024,517

[22] Filed: Feb. 17, 1998

[30] Foreign Application Priority Data

Feb. 17, 1997 [JP] Japan ................................. 9-048477
Feb. 18, 1997 [JP] Japan ................................. 9-049897

[51] Int. Cl.⁷ .............................. H04N 7/18; B65B 43/00
[52] U.S. Cl. .............................. 348/91; 348/92; 348/125; 209/938; 209/939; 53/900
[58] Field of Search .................................. 348/86, 91–92, 348/125; 209/938–939, 688–689, 690; 53/235, 240, 266.1, 285, 291, 900

[56] References Cited

U.S. PATENT DOCUMENTS

| | | | |
|---|---|---|---|
| 4,964,262 | 10/1990 | Moser et al. | 53/506 |
| 5,018,335 | 5/1991 | Yamamoto et al. | 53/281 |
| 5,348,062 | 9/1994 | Hartzell et al. | 53/900 X |
| 5,463,839 | 11/1995 | Stange et al. | 53/54 |
| 5,743,069 | 4/1998 | Ansaloni | 53/282 |
| 5,746,323 | 5/1998 | Dragotta | 209/539 |
| 5,836,141 | 11/1998 | Sundberg | 53/468 |
| 5,966,910 | 10/1999 | Ribani et al. | 53/560 |
| 6,009,690 | 1/2000 | Rosenberg et al. | 53/56 |

*Primary Examiner*—Vu Le

[57] ABSTRACT

Disclosed is an appearance inspecting device for a solid formulation, including a supply section for continuously supplying solid formulations such as capsules; an inspecting drum for holding on its outer peripheral portion the solid formulations supplied from the supply section, carrying the solid formulations in such a manner as to allow the solid formulations to be intermittently revolved, and allowing the solid formulations to be rotated on their axes at a specific carrying position; an image pickup device for photographing surfaces of the solid formulations being thus rotated on their axes; a quality determining section for processing images of the solid formulations thus picked up from the image pickup device and determining whether the solid formulations are nondefective or defective; and a classifying section for classifying the solid formulations into defective and nondefective solid formulations on the result determined by the quality determining section and recovering the defective and nondefective capsules. The inspecting device is capable of achieving a high inspection accuracy being sufficiently satisfied in terms of practical use, and also of performing length inspection for a solid formulation.

4 Claims, 9 Drawing Sheets

APPEARANCE INSPECTING DEVICE FOR SOLID FORMULATION

BACKGROUND OF THE INVENTION

The present invention relates to an appearance inspecting device for inspecting appearances of solid formulations each having a shape being rotation-symmetric around a specific axis, and particularly to an appearance inspecting device suitable for inspecting appearances of capsules in each of which a hard capsule piece having a cap and a body is filled with a medicine or appearances of empty capsules in each of which a cap and a body are only temporarily connected to each other before being filled with a medicine. In more particular, the present invention relates to an appearance inspecting device capable of inspecting solid formulations to be inspected at high accuracies by photographing the solid formulations using an image pickup device while rotating the solid formulations in accurately positioned states.

Conventionally, as an appearance inspecting device for automatically inspecting appearances of solid formulations such as capsules or elliptical ball-like tablets, various types have been proposed, and in recent years, visual inspection for solid formulations by a worker is being perfectly shifted to automatic inspection for solid formulations using such an automatic inspecting device. The appearance inspecting device of this automatic type is known, for example, from Japanese Patent Laid-open No. Hei 7-35693.

The appearance inspecting device disclosed in Japanese Patent Laid-open No. Hei 7-35693, having a configuration shown in FIGS. 6 to 8, is mainly used to inspect appearances of capsules in each of which a hard capsule piece having a cap and a body is filled with a medicine.

As shown in FIG. 6, this appearance inspecting device includes a supply hopper 2, a supply drum 3, a first direction restricting drum 4 and a second direction restricting drum 5, an inspecting drum 6, an image pickup device 7, a quality determining section 8, and a classifying/recovering section (not shown). The supply hopper 2 is adapted to contain a predetermined number of capsules and sequentially supply the capsules. The supply drum 3 is adapted to align the capsules supplied from the supply hopper 2 in upright states with axial lines of the capsules directed up and down (hereinafter, referred to simply as "upright states") and to supply the capsules thus aligned to the first and second direction restricting portions 4 and 5. The first and second direction restricting sections 4 and 5 are adapted to restrict directions of the capsules supplied from the supply drum 3 in laterally-turned states with the axial lines of the capsules directed in the horizontal direction (hereinafter, referred to simply as "laterally-turned states") and also with the cap sides thereof directed in a specific direction. The inspecting drum 6 is adapted to carry the capsules thus direction-restricted while holding the capsules on an outer peripheral portion thereof and to rotate the capsules in the course of carrying the capsules. The image pickup device 7 is adapted to photograph the capsules rotated while being held on the outer peripheral portion of the inspecting drum 6 and to pick up images of the capsules. The quality determining section 8 is adapted to process the images thus picked up by the image pickup device 7 and to determine whether the capsules are defective or nondefective. The classifying/recovering section is adapted to classify the capsules supplied from the inspecting drum 6 into nondefective capsules and defective capsules on the basis of the results determined by the quality determining section 8. In addition, in this specification, the term "up and down" for the capsules held on the outer peripheral portion of each drum means that the "up" side is equivalent to the outer peripheral side along the radial direction of the drum and the "down" side is equivalent to the center side along the radial direction of the drum; and the term "horizontal direction" for the capsules held on the outer peripheral portion of each drum means the direction perpendicular to the radial direction of the drum. That is, the "up and down" and the "horizontal direction" in this specification are not necessarily identical to the [up and down] and the [horizontal direction] based on the gravity direction.

The supply drum 3 is rotated around a horizontal axis A1 at a specific rotational speed, and it has on an outer peripheral surface thereof a plurality of supply pockets 31 for containing capsules at upright states. To prevent falling of the capsules contained in the supply pockets 31 therefrom, a falling preventive plate 32 is disposed to cover a lower side one-fourth portion of the outer periphery of the supply drum 3.

The supply hopper 2 is disposed over the supply drum 3. A lower end surface of the supply hopper 2 is partially in proximity to the outer peripheral surface of the supply drum 3, and part of the lower end surface of the supply hopper 2 is opened to the outer peripheral surface of the supply drum 3. A plurality of guide projection ribs 21, spaced at specific intervals, vertically project from a bottom portion of the supply drum 2. Between these guide projection ribs 21 are formed guide grooves 22 for aligning capsules. The guide grooves 22 are disposed at positions corresponding to those of the supply pockets 31 of the supply drum 3. The width of the guide groove 22 is slightly wider than a diameter of each capsule and is narrower than a length of a capsule. Accordingly, capsules pass through the guide grooves 22 with axial lines thereof directed in the length direction of the guide grooves 22, being inserted in the supply pockets 31 of the supply drum 3 with either of axial ends of the capsules being at the head, and are contained in the supply pockets 31 in the upright states.

The supply hopper 2 is usually vibrated by a vibration generator (not shown) for allowing the capsules in the supply hopper 2 to be smoothly contained in the supply pockets 31 of the supply drum 3 through the guide grooves 22. The capsules, which are not contained in the supply pockets 31 and are moved on an outer peripheral surface of the supply drum 3, are ejected from the surface of the supply drum 3 by a brush 23 disposed on the supply drum 3 along an edge portion of the supply hopper 2 and are returned again in the supply hopper 2.

The first direction restricting drum 4 is disposed under the supply drum 3 in such a state that an outer peripheral surface thereof is in proximity to the outer peripheral surface of the supply drum 3. The first direction restricting drum 4 is rotated around a horizontal axis A2 at a specific speed in the rotational direction reversed to that of the supply drum 3. A plurality of first direction restricting pockets 41 are formed in the outer peripheral surface of the first direction restricting drum 4 in such a state as to be aligned at positions corresponding to those of the supply pockets 31 of the supply drum 3. As shown in FIG. 8, the first direction restricting pockets 41 are composed of oblong-like upper portions 41a and vertical cylinder-like lower portions 41b formed on bottom surfaces at one-end portions of the upper portions 41a. The oblong-like upper portion 41a is allowed to perfectly contain a capsule in the laterally-turned state, and the vertical cylinder-like lower portion 41b is allowed to receive only the body of a capsule, that is, not to receive the cap thereof. With this configuration, the first direction restricting pocket 41 can perfectly contain a capsule C1 in the laterally-turned state and a capsule C2 in an upright state with the axial line thereof directed up and down and with the cap directed upward (hereinafter, referred to as "an upright state with the cap directed upward"); however, the first direction restricting pocket 41 cannot perfectly contain a capsule C3 in an upright state with the axial line thereof up and down and with the body directed upward (hereinafter, referred to as "an upright state with the body directed upward"), that is, it receives the capsule C3 in a state in which the body portion projects from the outer peripheral portion of the first direction restricting drum 4.

As shown in FIG. 6, a guide plate 42 is disposed in the vicinity of the outer peripheral surface of the first direction restricting drum 4 in such a manner as to partially surround the outer peripheral surface of the first direction restricting drum 4. A plurality of guide grooves 43 functioning as first direction restricting guides, in each of which one end is open and the other end is closed, are disposed on the guide plate 42 at positions corresponding to those of the first direction restricting pockets 41 of the first direction restricting drum 4. One inner edge portion of the guide groove 43 constitutes a pushing portion 43a tilted at a specific angle from the rotational direction of the first direction restricting drum 4. The pushing portion 43a is adapted to push the end portion of the body side of the capsule C3 (see FIG. 8) projecting from the outer peripheral surface of the first direction restricting drum 4, to thus laterally turn it in the first direction restricting pocket 41.

The second direction restricting drum 5 is disposed under the first direction restricting drum 4 in such a state that an outer peripheral surface thereof is in proximity to the outer peripheral surface of the first direction restricting drum 4. The second direction restricting drum 5 is rotated around a horizontal axis A3 at a specific speed in the rotational direction reversed to that of the first direction restricting drum 4. A plurality of second direction restricting pockets 51 are formed in the outer peripheral surface of the second direction restricting drum 5 in such a state as to be aligned at positions corresponding to those of the first direction restricting pockets 41 of the first direction restricting drum 4. As shown in FIG. 8, the second direction restricting pocket 51 is an oblong-like pocket which can perfectly contain the capsule C1 in the laterally-turned state and which receives the capsule C3 in the upright state in a state in which the end portion of the body side thereof projects from the outer peripheral surface of the second direction restricting drum 5. In this pocket 51, a bottom wall thereof is tilted downward to one end side, so that the capsule is contained in the pocket 51 in a state being shifted to the one end side.

As shown in FIG. 6, a guide plate 52 similar to the above guide plate 42 disposed along the outer periphery of the first direction restricting drum 4 is also disposed in the vicinity of the outer peripheral surface of the second direction restricting drum 5. While not shown, a plurality of guide grooves provided in the guide plate 52 constitute second direction restricting guides. The guide groove is adapted to laterally push the end portion of the body side of the capsule C3 projecting from the outer peripheral surface of the second direction restricting drum 5, to thus laterally turn the capsule C3 in the second direction restricting pocket 51.

The above drums 3, 4 and 5 are rotated, as shown typically in FIG. 6, by a motor M1 and a timing belt B in the direction shown by an arrow in FIG. 6 at such a timing as to allow the pockets 31, 41, and 51 to be aligned to each other.

The supply hopper 2, supply drum 3, first direction restricting drum 4, and second direction restricting drum 5 constitute a supply section for supplying capsules, as objects to be inspected, to the inspecting drum 6. In this case, capsules supplied from the supply hopper 2 at random are aligned in upright states by the supply drum 3, being all direction-restricted in laterally-turned states with cap sides thereof directed in a specific direction by the first and second direction restricting drums 4 and 5, and are supplied to the inspecting drum 6.

The inspecting drum 6 is disposed under the second direction restricting drum 5 in such a state that an outer peripheral surface is in proximity to the outer peripheral surface of the second direction restricting drum 5. The inspecting drum 6 is intermittently rotated around a horizontal axis A4 at a specific speed in the rotational direction reversed to that of the second direction restricting drum 5. The inspecting drum 6 includes a pair of disk-like flanges 61 oppositely spaced at a specific gap, and a plurality of first inspecting rollers 62a and a plurality of second inspecting rollers 62b which are rotatably provided between the flanges 61.

As shown in FIG. 7, both the flanges 61 are fixed on both end portions of an intermittently rotatable body 65 rotatably supported around a non-rotatable shaft 64 fixed on a frame 63. The intermittently rotatable body 65 is fixedly connected to a flange 66a formed on a base end side of an intermittently rotatable shaft 66 rotatably supported around a central portion of the non-rotatable shaft 64, and is rotatable integrally with the intermittently rotatable shaft 66. The intermittently rotatable shaft 66 is connected to an intermittently driving device D, to be thus intermittently rotated by the device D. Thus, the intermittently rotatable body 65 and the flanges 61 are rotated integrally with the intermittently rotatable shaft 66.

The first inspecting rollers 62a and the second inspecting rollers 62b are alternately disposed along the peripheral surface of the inspecting drum 6 in a state in which outer peripheral surfaces of both the rollers 62a and 62b are in proximity to each other. The rollers 62a and 62b are rotatably mounted between peripheral edge portions of the flanges 61. One-end portions of shafts 621a and 621b of the first and second inspecting rollers 62a and 62b pass through one of the flanges 61 and project outward therefrom, and planetary gears 622 are fixed to the projecting end portions of the shafts 621a and 621b. The planetary gears 622 are meshed with a sun gear 623 rotatably mounted on a base end portion of the intermittently rotatable shaft 66. A pulley 624 fixed on the sun gear 623 is connected to another pulley 625 mounted on a rotational shaft of a motor M2 through a timing belt 626. With this configuration, the sun gear 623 is rotated by the motor M2 through the timing belt 626 and the planetary gears 622 are rotated around the sun gear 623, so that the first and second inspecting rollers 62a and 62b integrated with the planetary gears 622 are rotated at a specific speed independently from the intermittent rotation of the flanges 61. To be more specific, the first and second inspecting rollers 62a and 62b are rotated on their axes while being revolved together with the flanges 61. In addition, the rotational direction of the first inspecting roller 62a is the same as that of the second inspecting roller 62b.

Capsules C4 supplied from the second direction restricting drum 5 in the state being direction-restricted are placed and held between the first and second inspecting rollers 62a and 62b, and are revolved around the non-rotatable shaft 64 while being rotated on their axes by the revolution and rotation of the first and second inspecting rollers 62a and 62b.

In this case, a plurality of flange portions 62c are formed on outer peripheral surfaces of the first inspecting rollers 62a in such a manner as to be spaced at equal intervals. As shown in FIG. 9, the capsules C4 are rotated on their axes and revolved in a state being held between the flanges portions 62c. Further, as shown in FIG. 7, nozzles 651 are formed in the intermittently rotatable body 65 at positions corresponding to the portions for holding the capsules. Besides, a suction cavity portion 641 communicated to a suction device (not shown) such as a vacuum pump is formed in the non-rotatable shaft 64 in such a manner as to extend nearly around a semi-periphery of the non-rotatable shaft 64, and compressed air flow passages 642 communicated to a compressed air supply device (not shown) such as a compressor are formed at positions corresponding to a defective capsule recovery can 71 (see FIG. 6) and a nondefective capsule recovery chute 72 (see FIG. 6). The nozzles 651 are sucked in vacuum through the suction cavity portion 641 to certainly hold the capsules C4 by the suction force, and compressed air is jetted from the nozzles 651 through the compressed air flow passages 642 to blow the capsules C4 into either the defective capsule recovery can 71 or nondefective capsule recovery chute 72 by the compressed air.

The appearance inspection for capsules using such a related art appearance inspecting device is performed as follows: First, a-predetermined number of capsules charged in the supply hopper 2 are sequentially supplied into the supply drum 3 in the upright states by the above-described action, being contained in the upright states in the supply pockets 31 formed in the outer peripheral surface of the supply drum 3, and carried downward by the rotational motion of the supply drum 3.

As shown in FIG. 8, when reaching the lowermost portion of the supply drum 3, the capsules are transferred from the supply drum 3 to the first direction restricting pockets 41 of the first direction restricting drum 4. At this time, the capsules C2 transferred in the upright states with the caps thereof directed upward are nearly perfectly contained in the pockets 41 in the states in which the body portions are inserted in the lower portions 41b of the first direction restricting pockets 41. On the other hand, the capsules C3 transferred in the upright states with the caps directed downward are received in the pockets 41 in the states in which the body portions project from the outer peripheral surface of the first direction restricting drum 4 because the cap portions are not inserted in the lower portions 41b of the first direction restricting pockets 41.

These capsules C2 and C3 are carried downward in these states by rotation of the first direction restricting drum 4. At this time, the capsules C2 nearly perfectly contained in the first direction restricting pockets 41 are carried to the lowermost portion of the drum 4 as left in these postures. Besides, with respect to the capsules C3 with the body portions projecting from the outer peripheral surface of the drum 4, the body portions are inserted in the guide grooves 43 of the guide plate 42 (see FIG. 6) and are laterally pushed by the pushing portions 43a of the guide grooves 43 (see FIG. 6). As a result, the capsules C3 are laterally turned in the first direction restricting pockets 41 and are carried to the lowermost portion of the drum 4 as the capsules C1 in the laterally-turned states with the caps directed in one direction (right side in FIG. 8).

Next, as shown in FIG. 8, when reaching the lowermost portion of the first direction restricting drum 4, these capsules C2 and C1 are transferred from the drum 4 to the second direction restricting pockets 51 of the second direction restricting drum 5. At this time, the capsules C1 in the laterally-turned states are nearly perfectly contained in the second direction restricting pockets 51 as left in the laterally-turned states. On the other hand, the capsules C2 in the upright states with the caps directed upward are transferred in the second direction restricting pockets 51 with the cap sides being at the head and thereby they are turned over in the vertical direction. In other words, the capsules C2 are transferred in the second direction restricting pockets 51 as the capsules C3 in the upright states with the bodies directed upward. With respect to the capsules C3, the body portions project from the outer peripheral surface of the second direction restricting drum 5.

The capsules C1 and C3 in these states are carried downward by rotation of the second direction restricting drum 5. At this time, the capsules C1 in the laterally-turned states, which are nearly perfectly contained in the second direction restricting pockets 51, are carried to the lowermost portion of the drum 5 as left in the postures. Beside, the capsules C3 with the body portions projecting from the outer peripheral surface of the drum 5 are laterally turned in the second direction restricting pockets 51 in the same manner as described above by the action of the guide grooves (not shown) of the guide plate 52 (see FIG. 6) to be converted into the capsules C4 in the laterally-turned states with the caps directed in one direction (right side, in the figure), and are carried to the lowermost portion of the drum 5. Thus, both the capsules C1 and C3 are converted into the capsules C4 in the laterally-turned states with the caps directed in one direction (right side, in the figure), and are transferred onto the first and second inspecting rollers 62a and 62b of the inspecting drum 6.

In addition, as shown in FIG. 8, upon transfer of the capsules between the drums 3, 4, 5 and 6, compressed air is supplied to respective pockets on the delivery side to push out the capsules while portions of respective pockets and rollers 62a on the receiving side are sucked in vacuum to attain smooth transfer of the capsules.

The capsules C4 supplied to the inspecting drum 6 in the state being direction-restricted are, as described above, placed and held between the first and second inspecting rollers 62a and 62b, and are carried downward by intermittent rotation of the inspecting drum 6 while being rotated by rotation of the first and second inspecting rollers 62a and 62b. In this case, as shown in FIG. 9, the capsules C4 are carried while being rotated in the state being held between the flange portions 62c of the first inspecting rollers 62a, and at this time, the capsules C4 are sucked and held between both the inspecting rollers 62a and 62b by the above-described sucking mechanism.

The capsules C4 thus held and carried by the inspecting drum 6 in the states being direction-restricted are photographed by the image pickup device 7 (see FIG. 6) during a period for which the rotation of the inspecting drum 6 is stopped at a specific position in the course of carrying of the capsules C4. At this time, each capsule C4 is rotated at least one turn or more at a specific speed by rotation of the first and second inspecting rollers 62a and 62b, so that the entire peripheral surface of the capsule C4 is photographed by the image pickup device 7. After photographing, the capsules C4 are carried to the lowermost portion of the inspecting drum 6 by intermittent rotation of the inspecting drum 6 while being held between the first and second inspecting rollers 62a and 62b.

The image of each capsule C4 picked up by the image pickup device 7 is processed by the above quality determining section 8 (see FIG. 6). The quality determining section 8 determines a quality of each capsule C4 by detecting whether the appearance of the capsule C4 is defective or nondefective. On the basis of the determined result, each capsule C4 is blown down either in the defective capsule recovery can 71 or in the nondefective capsule recovery chute 72 by the above-described compressed air jetting means. The capsules are thus classified into defective and nondefective capsules and are recovered.

In this case, a position at which the capsule being defective in appearance is to be blown down in the defective capsule recovery can 71 is before the nondefective capsule recovery chute 72. At such a position, compressed air is jetted on the basis of an instruction supplied from the quality determining section 8. That is, at the position before the nondefective capsule recovery chute 72, only the capsule judged to be defective by the above determined result is blown down by compressed air. On the other hand, at a position where a nondefective capsule is to be blown down into the nondefective capsule recovery chute 72, compressed air is usually jetted to all of the capsule holding portions. All of the capsules C4 reaching such a position are thus blown down in the nondefective capsule recovery chute 72. In summary, the capsules defective in appearance are ejected from the inspecting drum 6 at the position before the nondefective capsule recovery chute 72 and recovered into the defective capsule recovery can 72, and only the capsules not defective in appearance are discharged from the nondefective capsule recovery chute 72 to the outside of the inspecting device.

In this way, according to the related art appearance inspecting device, appearances of capsules can be perfectly automatically inspected by the steps of aligning capsules charged at random with caps thereof being directed in a specific direction, photographing the capsules thus direction-restricted by the image pickup device while rotating the capsules, determining whether the appearances of the capsules are defective or nondefective on the basis of the images thus obtained, and classifying the capsules into nondefective and defective capsules and recovering the nondefective and defective capsules.

The related art appearance inspecting device, however, has been insufficient in terms of inspecting accuracy, and it has not been practically used from the viewpoint of inspecting performances.

To be more specific, in the above-described related art appearance inspecting device, as shown in FIG. 9, the capsule C4 is positioned in a state being held between the flange portions 62c of the first inspecting roller 62a, and in such a state, an image of the capsule C4 is photographed by the image pickup device 7. In this case, since the width "W" between the flange portions 62c is set to be slightly wider than the length "L" of the capsule C4 in order to certainly smoothly perform transfer of the capsule C4 from the second direction restricting drum 5, the capsule C4 held between the flanges 62c are rotated while being finely moved or vibrated in the axial direction, as a result of which, the image of the capsule cannot be picked up in a state in which the capsule is accurately positioned.

The image of the capsule thus obtained, therefore, contains not a little disturbance due to deviation of the capsule upon rotation thereof. Consequently, if qualities of capsules are strictly determined on the basis of image processing, most of capsules including a large number of nondefective capsules may be possibly determined to be defective. For this reason, a criterion for determining whether appearances of capsules are defective or nondefective must be set in consideration of the fact that deviation of capsules occurs to some extent. This makes it impossible to attain a high inspection accuracy. In particular, a stepped portion is necessarily formed on the surface of a capsule at a boundary between a cap and a body, and a failure such as a fine split-like damage or crack is liable to be produced in the vicinity of the stepped portion upon connection of the cap to the body. In general, to detect such a failure while identifying it from the stepped portion, there has been adopted a method in which a change in image data due to the stepped portion is previously stored and an abnormality different from the change thus stored is recognized as defective in appearance. In the case where the stepped portion is irregularly moved by deviation of the capsule, however, it is substantially impossible to previously accurately estimate and store a change in image data due to the stepped portion, and since a position on an image at which a change in data due to the stepped portion occurs cannot be specified, it is very difficult to detect a failure such as a damage or crack at a boundary between a cap and a body while identifying it from the stepped portion. It should be noted that in the case where a band seal is attached to a boundary between a cap and a body, the same problem also occurs.

Further, in capsules, the connection lengths between caps and bodies are not necessarily specified depending on manufacturing factors, and accordingly, the lengths L of the capsules are varied somewhat, that is, not specified. For this reason, the width "W" between the above flanges 62c (see FIG. 9) must be set wide with an appreciable allowance. And, in the case where a capsule having an entire length L being so relatively short as not to be defective is held between the flanges 62c which are set such that the width "W" is relatively wider with the appreciable allowance as described above, deviation of the capsule during rotation thereof becomes significant, and in such a case, it is impossible to normally perform appearance inspection for the capsule.

Further, although a capsule with its length L over a specific allowance range must be ejected as a defective capsule because the filling amount of a medicine is varied or connection between a cap and a body is insufficient, the related art appearance inspecting device fails to actually inspect the capsule being defective in length because the capsule is rotated while being moved or vibrated in the axial length, that is, in the length direction as described above and the capsule is subjected to appearance inspection in the condition that such a deviation is allowed.

SUMMARY OF THE INVENTION

In view of the foregoing, the present invention has been made, and an object of the present invention is to provide an appearance inspecting device for a solid formulation, including a supply section for continuously supplying solid formulations such as capsules; an inspecting drum for holding on its outer peripheral portion the solid formulations supplied from the supply section, carrying the solid formulations in such a manner as to allow the solid formulations to be intermittently revolved, and allowing the solid formulations to be rotated on their axes at a specific carrying position; an image pickup device for photographing surfaces of the solid formulations being thus rotated on their axes; a quality determining section for processing images of the solid formulations thus picked up from the image pickup device and determining whether the solid formulations are nondefective or defective; and a classifying section for classifying the solid formulations into defective and nondefective solid formulations on the result determined by the quality determining section and recovering the defective and nondefective capsules, whereby the appearance inspecting device is capable of improving an inspecting accuracy of the appearance inspecting device for a solid formulation, thereby achieving a high inspection accuracy being sufficiently satisfied in terms of practical use, and also of performing length inspection for a solid formulation.

To achieve the above object, according to the present invention, there is provided an appearance inspecting device for inspecting appearances of solid formulations each having a shape being rotation-symmetric around a specific axis, including:

a supply section for continuously supplying the solid formulations;

an inspecting drum for holding on its outer peripheral portion the solid formulations supplied from the supply section and carrying the solid formulations in such a manner as to allow the solid formulations to be intermittently revolved, and rotating the solid formulations at a specific carrying position;

an image pickup device for photographing surfaces of the solid formulations rotated by the inspecting drum;

a quality determining section for processing images of the solid formulations picked-up by the image pick-up device and determining whether the solid formulations are defective or nondefective; and a classifying means for classifying the solid formulations into defective capsules and nondefective capsules on the basis of the results determined by the quality determining section and recovering the defective and nondefective capsules;

wherein the inspecting drum includes a fixed inner cylinder, and an outer cylinder rotatably mounted on an outer periphery of the inner cylinder in such a manner as to be intermittently rotated along the outer peripheral surface of the inner cylinder;

a roller rotatable on a rotational axis extending along the axial direction of the inner cylinder is provided inside a portion of the inner cylinder in a state in which a surface of the roller is exposed from the outer peripheral surface of the inner cylinder;

the surface of the roller, exposed from the outer peripheral surface of the inner cylinder, is formed into a cross-sectional shape being tiled downward to one axial end side; and the outer cylinder has lead-through holding pockets each being formed into an elliptic, oblong, or rectangular shape having a center axis offset a specific angle from the axial direction of the outer cylinder;

whereby the solid formulations are held in the lead-through holding pockets and carried by intermittent rotation of the outer cylinder; the solid formulations in the lead-through holding pockets intermittently stopped at a specific carrying position are rotated on the roller being rotated on the rotational axis; and outer peripheral surfaces of the solid formulations thus rotated are photographed by the image pickup device.

In the appearance inspecting device of the present invention, solid formulations such as capsules supplied from the supply section are contained in the lead-through holding pockets of the outer cylinder constituting the inspecting drum, and are carried by intermittent rotation of the outer cylinder in such a manner as to be intermittently revolved. In the course of carrying of the solid formulations, the solid formulations are rotated by the roller being rotated on its axis in the inspecting drum and are photographed by the image pickup device. From the images of the solid formulations thus obtained, it is determined by the quality determining section whether the solid formulations are defective or nondefective in appearance. On the basis of the determined results, the solid formulations are classified into defective and nondefective solid formulations, and are recovered.

In this case, according to the appearance inspecting device of the present invention, the inspecting drum includes the fixed inner cylinder and the outer cylinder intermittently rotatably mounted outside the inner cylinder, and the solid formulations are carried in the states being contained in the lead-through pockets provided in the outer cylinder intermittently rotated. As a result, the solid formulations are carried while being rolled on the outer peripheral surface of the inner cylinder in the states being held in the lead-through holding pockets.

When being carried up to the portion where the roller being rotatable on its axis is disposed and intermittently stopped, the solid formulations are placed on the surface of the roller exposed from the outer peripheral surface of the inner cylinder, and are then rotated by rotation of the roller within the lead-through holding pockets. To be more specific, the solid formulations are rotated so as to be rolled on the surface of the roller rotated on its axis in the states being held in the stopped lead-through holding pockets. The lead-through holding pocket for holding the solid formulation is formed in a state in which the center axis is offset a specific angle from the axial direction of the outer cylinder, and accordingly, the center axis of the lead-through holding pocket is also offset the specific angle from the rotational shaft of the roller disposed along the axial direction of the inner cylinder. As a result, the rotational shaft of the solid formulation which is rolled on the surface of the roller while being held in the lead-through holding pocket is offset from the rotational shaft of the roller. The solid formulation is thus rolled on the surface of the roller in the direction offset obliquely from the rotational direction of the roller in the state being held in the lead-through holding pocket. As a result, each solid formulation in the lead-through holding pocket is shifted to one end side of the pocket. Further, the surface of the roller is formed in such a cross-sectional shape as to be tilted downward to one axial end side, so that the solid formulation rotated on the tilted surface of the roller tends to be moved toward the one axial end side. That is, the solid formulation is rotated on the surface of the roller while certainly keeping the state in which the solid formulation is shifted to the one end side of the lead-through holding pocket.

In addition, since the center axis of the lead-through holding pocket is offset the specific angle from the axial direction of the outer cylinder, the solid formulation carried by rotation of the outer cylinder while being held in the lead-through holding pocket and rolled on the outer peripheral surface of the inner cylinder is rolled in the direction offset from the rotational direction of the outer cylinder, so that the solid formulation can be shifted on one end side of the lead-through holding pocket during a period for which the solid formulation is carried to the portion where the roller is disposed. In this case, by setting the end portion to which the solid formulation is shifted during carrying to be identical to the end portion to which the solid formulation is shifted during rotation on the roller, the solid formulation shifted on the one end side of the lead-through holding pocket during carrying is allowed to be rotated on the roller while keeping the state in which the solid formulation has been shifted on the one end side during carrying. In the inspecting device of the present invention, however, since the solid formulation can be, as described above, certainly moved (shifted) to the one end side of the lead-through holding pocket while being rotated on the roller, the direction in which the solid formulation is shifted during carrying may be set to be reversed to the direction in which the solid formulation is shifted on the roller.

In this way, according to the appearance inspecting device of the present invention, all of the solid formulation held by the inspecting drum can be positioned to be shifted to one end sides of the lead-through holding pockets, and the solid formulations are photographed in states being rotated while certainly keeping the positioned states. Accordingly, it is possible to certainly obtain clear images of the solid formulations without occurrence of disturbance such as deviation, and hence to inspect appearances of the solid formulations at high accuracies under a strictly determined quality criterion.

To inspect appearances of capsules in each of which a hard capsule piece having a cap and a body is filled with a medicine, there may be provided a suitable direction restricting means such as the same direction restricting means as that used for the related art appearance inspecting device. In this case, capsules are direction-restricted in laterally-turned states with the caps being directed in a specific direction, being supplied to the inspecting drum in these states, and are all positioned to be shifted to the cap sides in the lead-through holding pockets, followed by inspection of appearances of the capsules. As a result, it is possible to inspect an appearance of each capsule in a state that a stepped portion formed at a boundary between the cap and the body is accurately positioned. Thus, it is possible to detect a failure such as a fine split-like damage or crack liable to produced in the vicinity of the stepped portion of each capsule while certainly identifying it from the stepped portion in accordance with the related art method in which a change in image data due to the stepped portion is previously stored, and hence to easily attain a strict appearance inspection for capsules. For a capsule in which a band seal is attached to a boundary between a cap and a body, a failure such as a damage produced at the band seal portion can be detected while being certainly identified from the band seal in the same manner as described above.

To be more specific, for a capsule in which a cap and a body are connected to each other, a connection length between the cap and the body is varied, and thereby the entire length as of the capsule is not necessarily specified; however, since the length of the cap fitted around the body is usually specified. Accordingly, a boundary between the cap and the body can be accurately positioned by shifting the capsule to the cap side. Thus, a change in image data due to the above stepped portion can be accurately estimated and stored, and further a position on an image on which the change in data due to the stepped portion appears can be certainly specified, so that a failure such as a damage which occurs as an abnormality different from the change previously stored can be easily detected while being certainly identified from the above stepped portion.

Further, according to the appearance inspecting device of the present invention, as described above, since all of the solid formulations to be inspected are photographed in the states being shifted on one end sides in the lead-through holding pockets, one-ends of the capsules are lined up in images thus obtained so that lengths of the solid formulations can be accurately inspected by detecting the other ends of the solid formulations. As a result, the lengths of solid formulations can be inspected simultaneously with usual appearance inspection.

In this way, according to the appearance inspecting device for a solid formulation according to the present invention, it is possible to attain a high inspecting accuracy being sufficiently satisfied in terms of practical use, and also to perform length inspection simultaneously with usual appearance inspection. In addition, a solid formulation as an object to be inspected in the present invention has a shape being rotation-symmetric around a specific axis. Specific examples of the solid formulations may include a hard capsule, a soft capsule, and a tablet formed into an elliptic-ball or ball shape. In particular, the present invention is suitably used for inspecting appearances of hard capsules each of which has a cap and a body. In this case, the hard capsule may be of a type filled with a medicine or an empty type in which a cap and a body are temporarily connected before being filled with a medicine. In the case of inspecting appearances of empty capsules, the same effect as that obtained in the above-described appearance inspection for solid formulations can be obtained.

DETAILED DESCRIPTION OF THE PREFERRED EMBODIMENT

Hereinafter, the present invention will be more fully described by way of embodiment.

Figure 1:
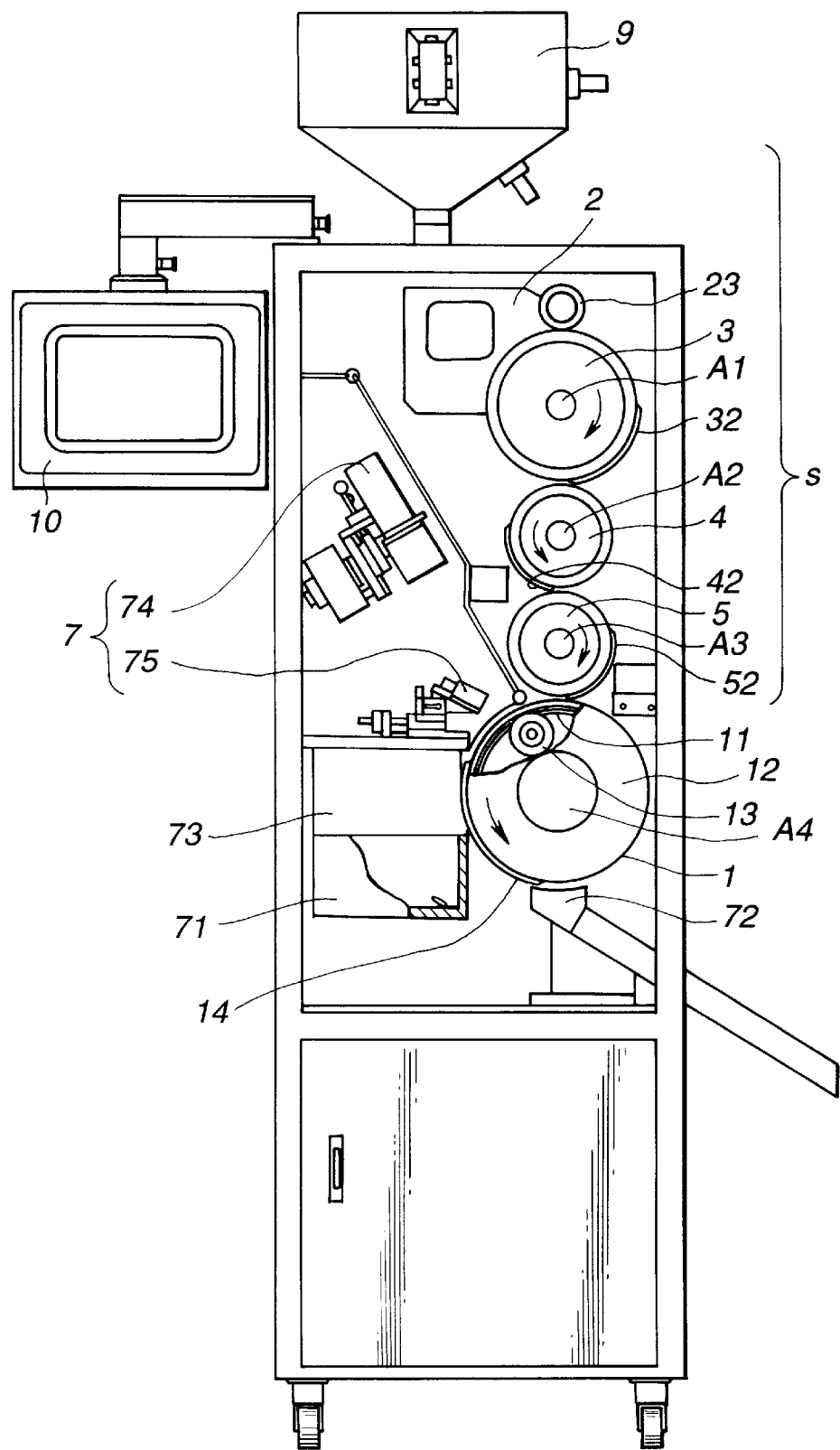
FIG. 1 is a schematic view showing an appearance inspecting device for a solid formulation according to one embodiment of the present invention.

FIGS. 1 to 5 show an appearance inspecting device according to one embodiment of the present invention. The appearance inspecting device is used to inspect appearances of capsules in each of which a hard capsule piece having a cap and a body is filled with a medicine and empty capsules in each of which a cap and a body are temporarily connected to each other before being filled with a medicine (hereinafter, these are referred to collectively as "capsules"). As shown in FIG. 1, the appearance inspecting device includes a supply hopper 2, a supply drum 3, a first direction restricting drum 4, a second direction restricting drum 5, an inspecting drum 1, a defective capsule recovery can 71, a nondefective capsule ejecting chute 72, an image pickup device 7, a quality determining section (not shown), and a classifying means (not shown).

The supply hopper 2, supply drum 3, first direction restricting drum 4, and second direction restricting drum 5 constitute a supply section "s" for supplying capsules to the inspecting drum 1. Capsules supplied at random from the supply hopper 2 are aligned in upright states at the supply drum 3, being all direction-restricted in laterally-turned states with the cap sides thereof being directed in a specific direction, and are supplied to the inspecting drum 1. It should be noted that the supply section "s" has the same configuration as that of the supply section of the above-described related art appearance inspecting device (see FIGS. 6 to 9) and performs supply and direction-restriction of capsules by the same action as that of the supply section of the related art appearance inspecting device. Accordingly, in this embodiment, with respect to the configuration and action of the supply section "s", components of the supply section "s" are indicated by the same reference numerals as those of the corresponding components of the related art appearance inspecting device (see FIGS. 6 to 9), and explanation thereof is omitted.

The inspecting drum 1 is equivalent to the inspecting drum 6 of the above-described related art appearance inspecting device (see FIGS. 6 to 9). The inspecting drum 1 holds on its outer peripheral portion capsules supplied from the second direction restricting drum 5 in the state being direction-restricted and carries the capsules downward in such a manner as to allow the capsules to be intermittently revolved. In the course of carrying of the capsules by the inspecting drum 1, the capsules are photographed by the image pickup device 7, and then separately blown into the defective capsule recovery can 71 and the nondefective capsule recovery chute 72 by the classifying means (not shown) provided in the inspecting drum 1.

Figure 2:
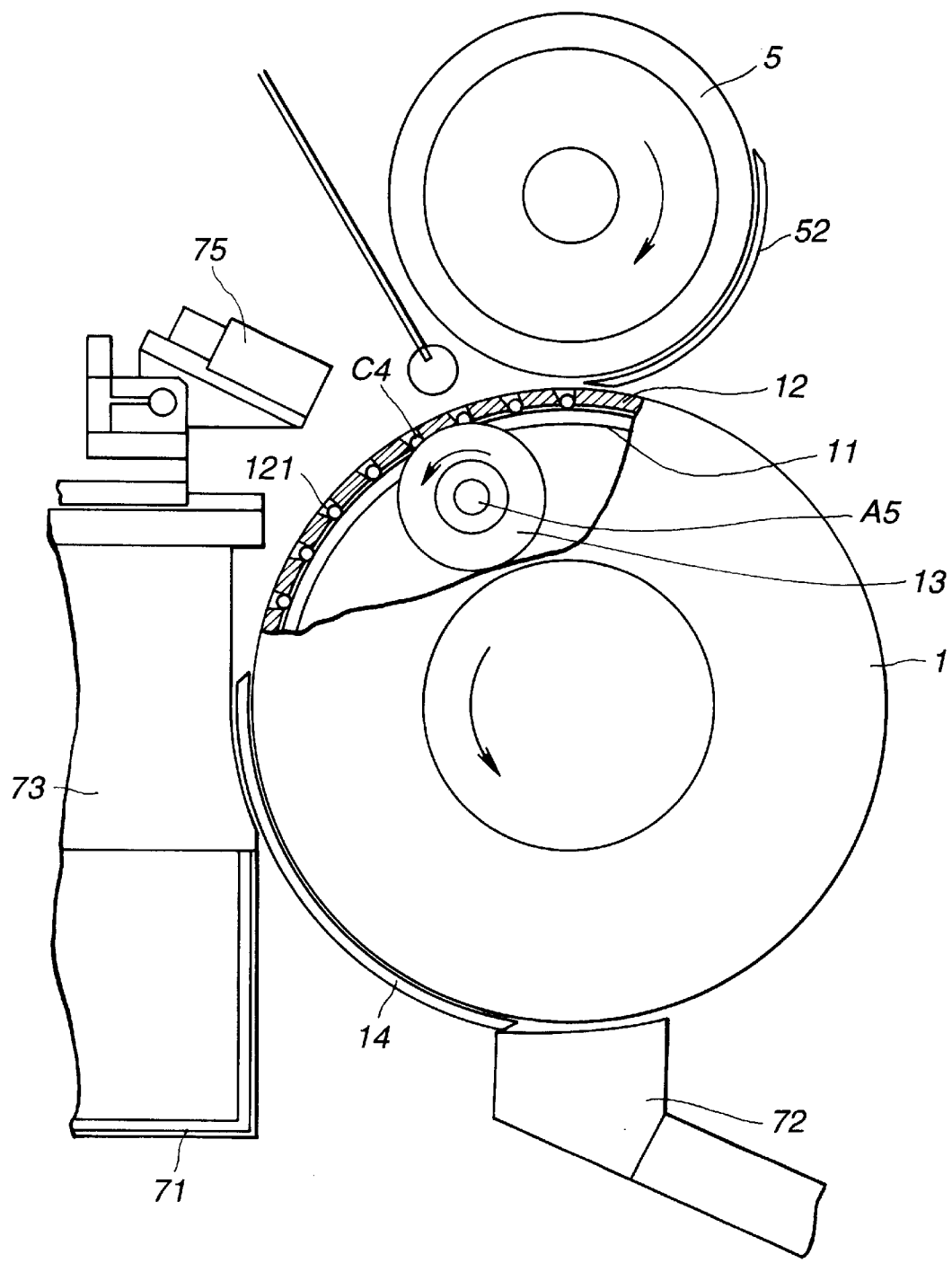
FIG. 2 is a schematic sectional view showing an inspecting drum portion of the appearance inspecting device shown in FIG. 1, with parts partially cutaway.
Figure 3:
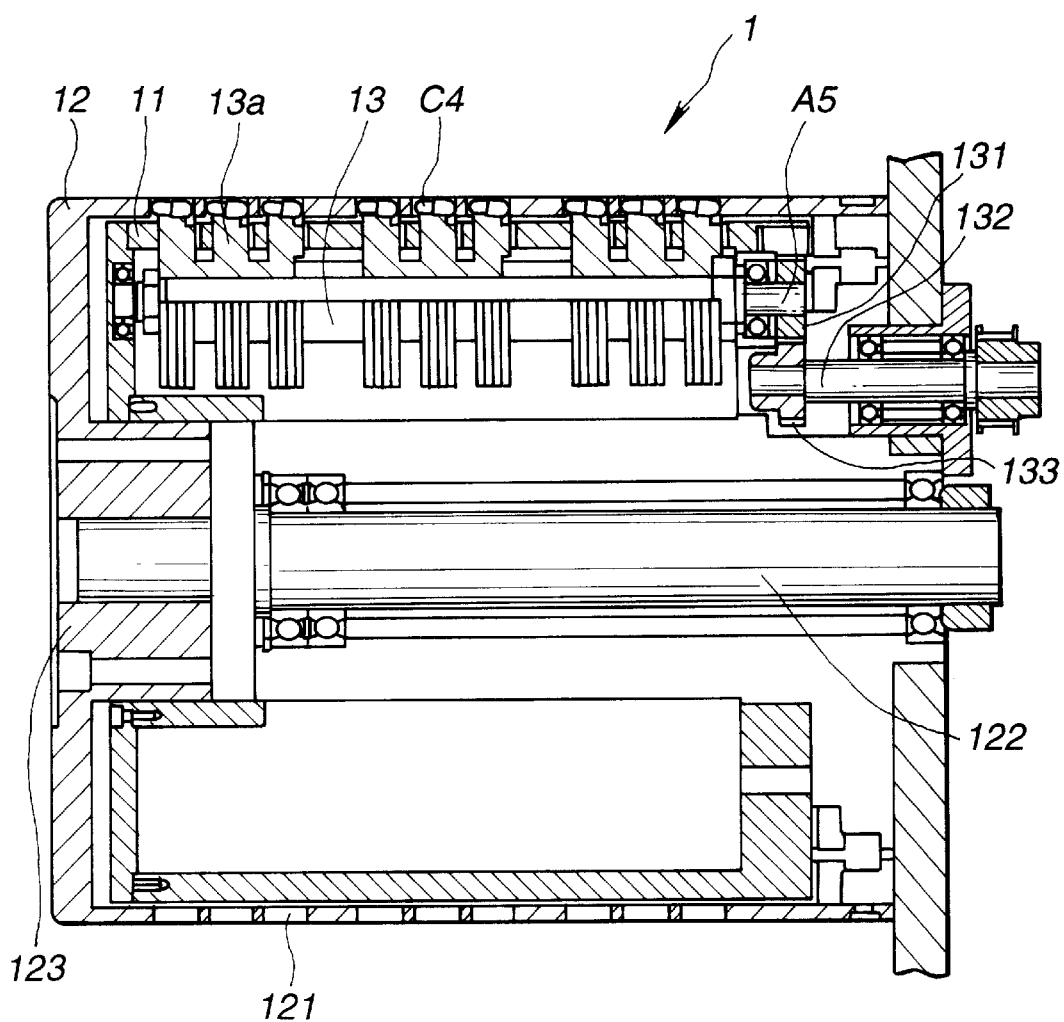
FIG. 3 is a sectional view showing an inspecting drum of the appearance inspecting device shown in FIG. 1.
Figure 4:
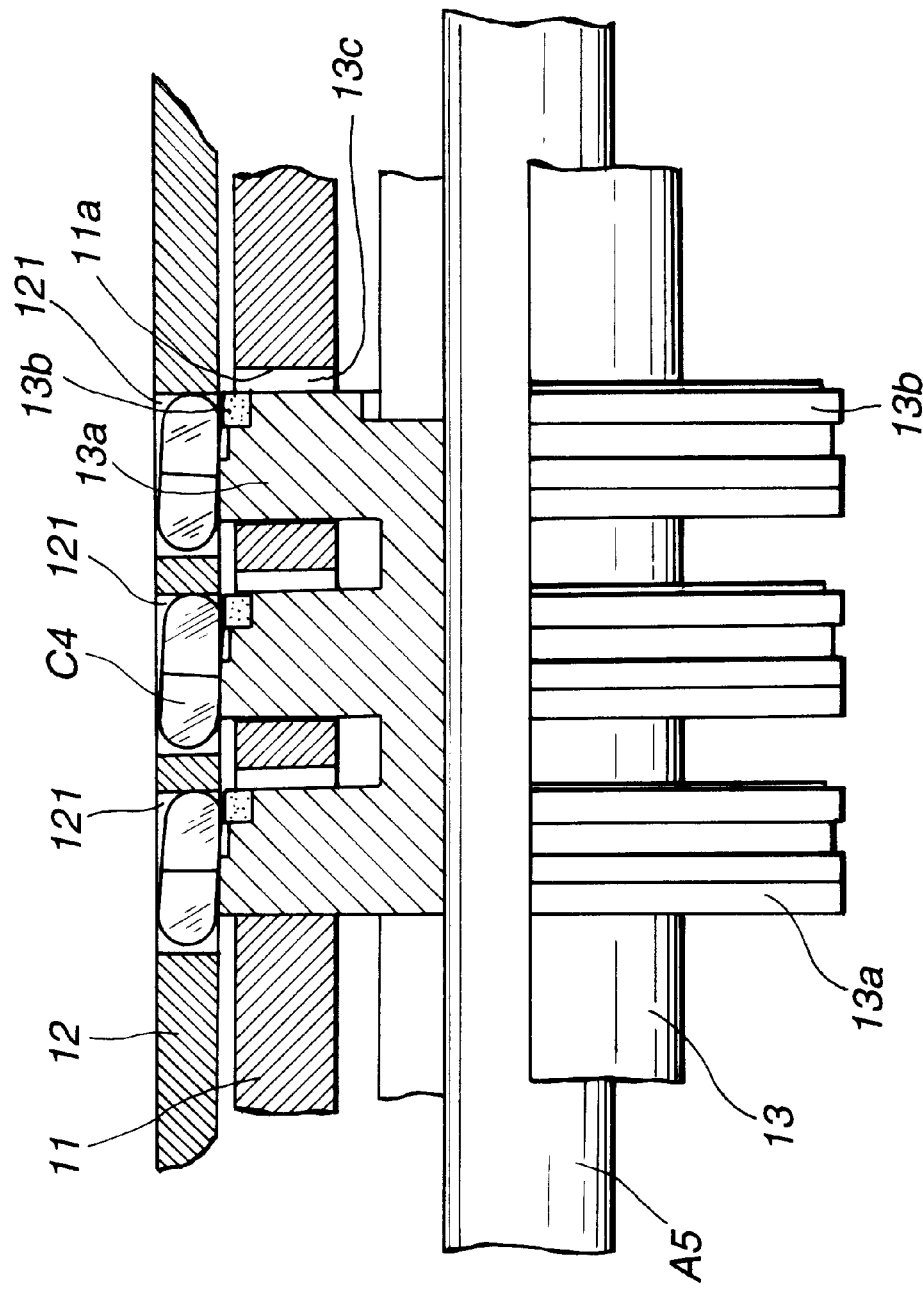
FIG. 4 is a partially enlarged sectional view showing a roller portion, being rotated on its axes, provided in the inspecting drum shown in FIG. 3.

As shown in FIGS. 2 to 4, the inspecting drum 1 in this embodiment includes a fixed inner cylinder 11 and a outer cylinder 12 rotatably mounted on an outer periphery of the inner cylinder 11.

A roller 13 is disposed inside the inner cylinder 11 in such a manner as to be rotated on its rotational shaft A5 extending in the axial direction of the inner cylinder 11. As shown in FIG. 4, a plurality of projecting rings 13a, each being formed in a thick flange-shape, are provided on the roller 13. Outer peripheral surfaces of the projecting rings 13a pass through a plurality of roller insertion windows 11a formed in the inner cylinder 11 and are exposed from an outer peripheral surface of the inner cylinder 11. A surface of the projecting ring 13a (roller surface) exposed from the outer peripheral surface of the inner cylinder 11 has a stepped portion at an intermediate portion in the axial direction, and is entirely tilted downward in cross-section toward one axial end side (right side, in the figure). A ring-like rubber member 13b is circumferentially mounted at the edge portion on the downward tilted side (right side, in the figure). In addition, the tilting angle of the surface of the projecting ring 13a (roller surface) is usually in a range of 3° to 5°.

A specific gap 13c is formed at a position on the downward tilted side (right side, in the figure) between an inner surface of the roller insertion window 11a and a side surface of the projecting ring 13a of the roller 13. In this case, the interior of the inner cylinder 11 is usually evacuated by a vacuum pump to suck the capsule C4 placed on the roller 13 through the gap 13c.

With respect to the roller 13 being rotatable on the rotational axis A5, as shown in FIG. 3, both end portions of the rotational shaft A5 are rotatably supported on both side walls of the inner cylinder 11. A gear 131 is mounted on the one end portion of the rotational shaft A5 and is meshed with a drive gear 133 fixed on a drive shaft 132 connected to a drive source such as a motor (not shown). Thus, the roller 13 is usually rotated around the rotational shaft A5 at a specific speed.

While not shown, compressed air jetting nozzles are provided at each of one side portion and the lowermost portion of a peripheral wall of the inner cylinder 11 at positions corresponding to those of lead-through holding pockets 121 (which will be described later) of the outer cylinder 12. The nozzles provided at the one side portion are used for blow defective capsules into the defective capsule recovery can 71 (see FIGS. 1 and 2), and they are operated to jet compressed air on the basis of an instruction of the quality determining section. Besides, the nozzles provided at the lowermost portion are used to blow nondefective capsules into the nondefective capsule recovery chute 72, and they are operated to usually jet compressed air. Hereinafter, the nozzles provided on the one side portion are referred to as "defective capsule ejecting nozzles", and the nozzles provided at the lowermost portion are referred to as "nondefective capsule ejecting nozzles".

Figure 5:
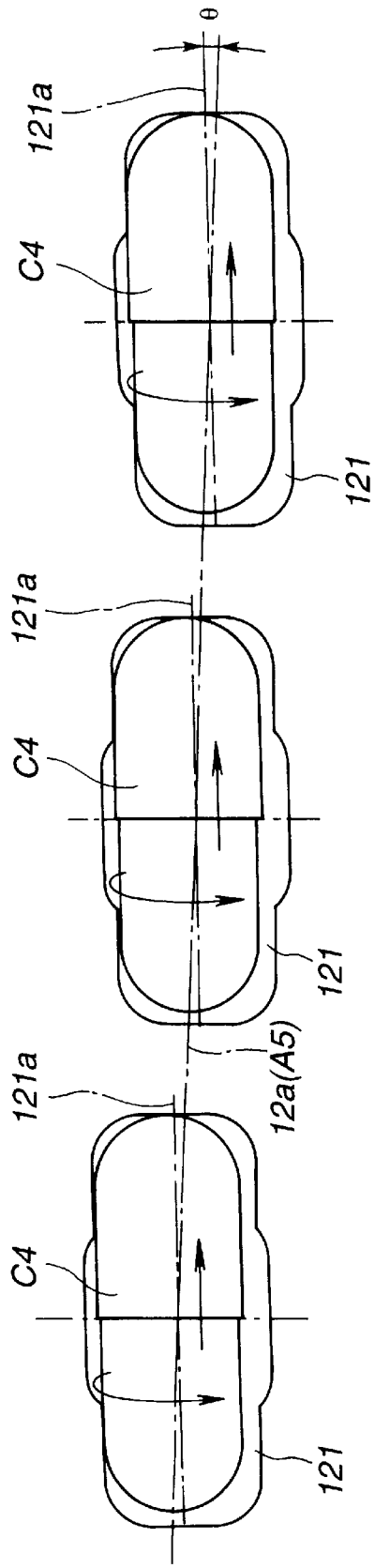
FIG. 5 is a view illustrating an action of a capsule contained in a lead-through holding pocket provided in an outer cylinder of the inspecting drum shown in FIG. 3.
Figure 6:
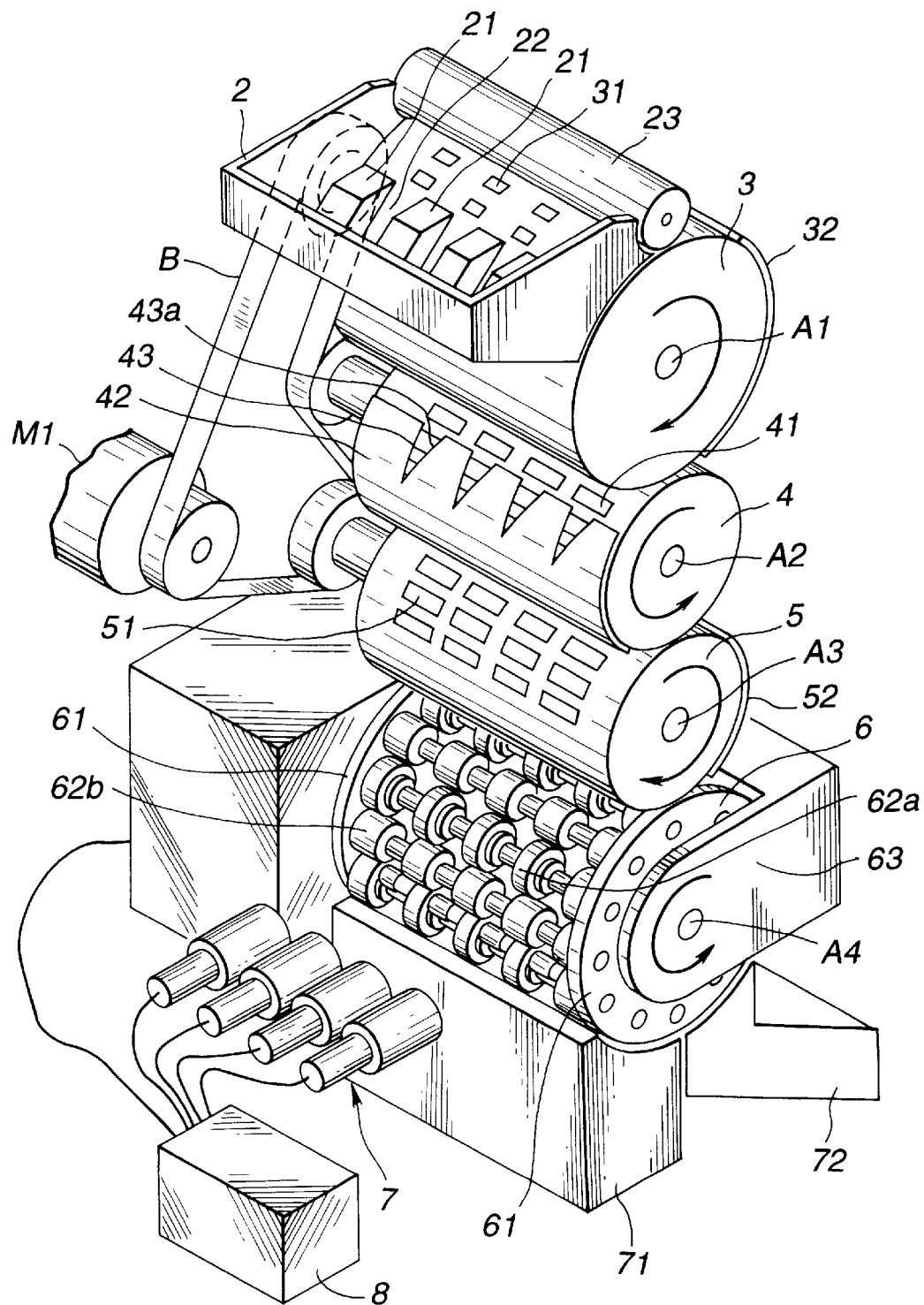
FIG. 6 is a schematic perspective view showing a related art appearance inspecting device.
Figure 7:
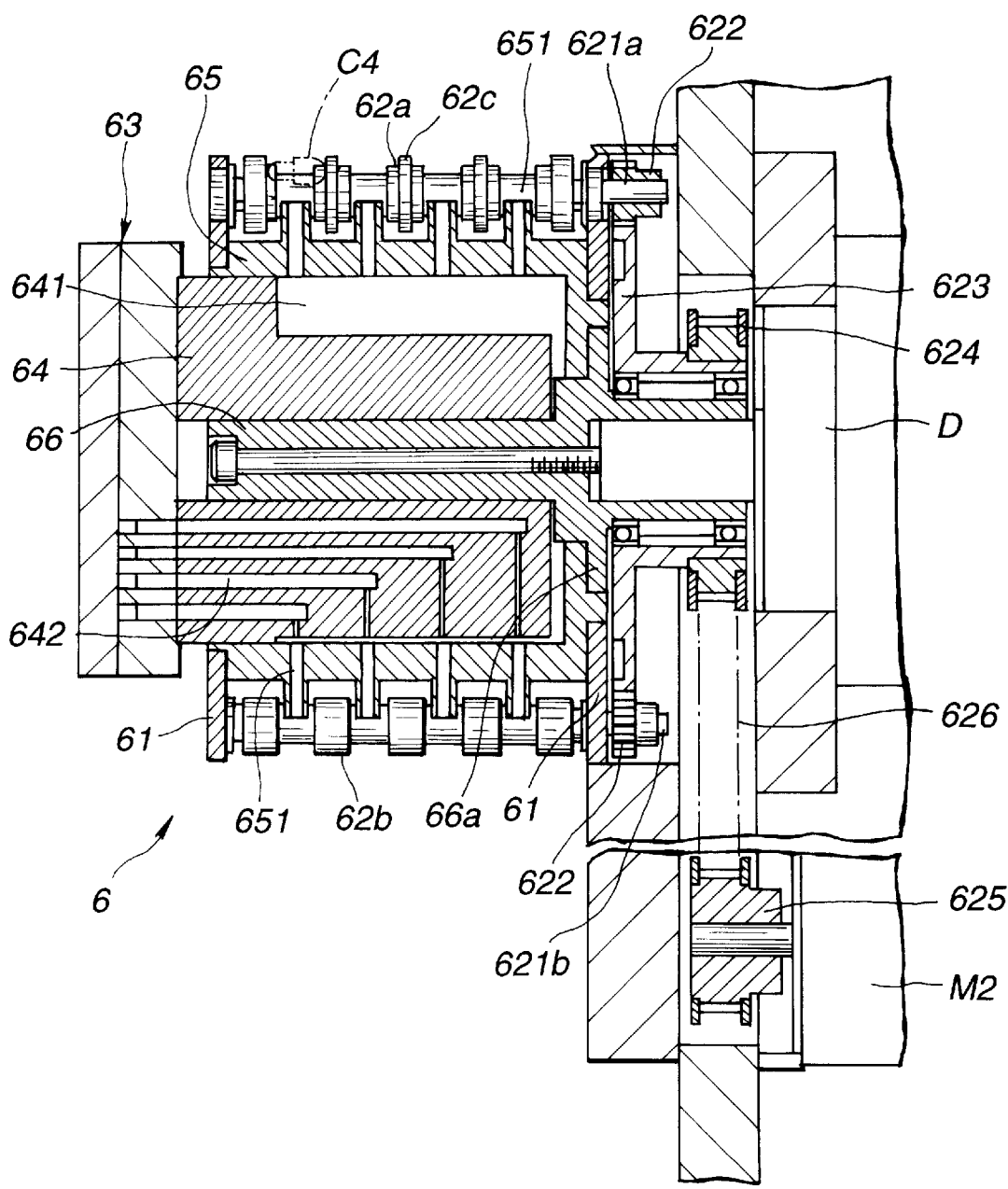
FIG. 7 is a sectional view showing an inspecting drum of the appearance inspecting device shown in FIG. 6.
Figure 8:
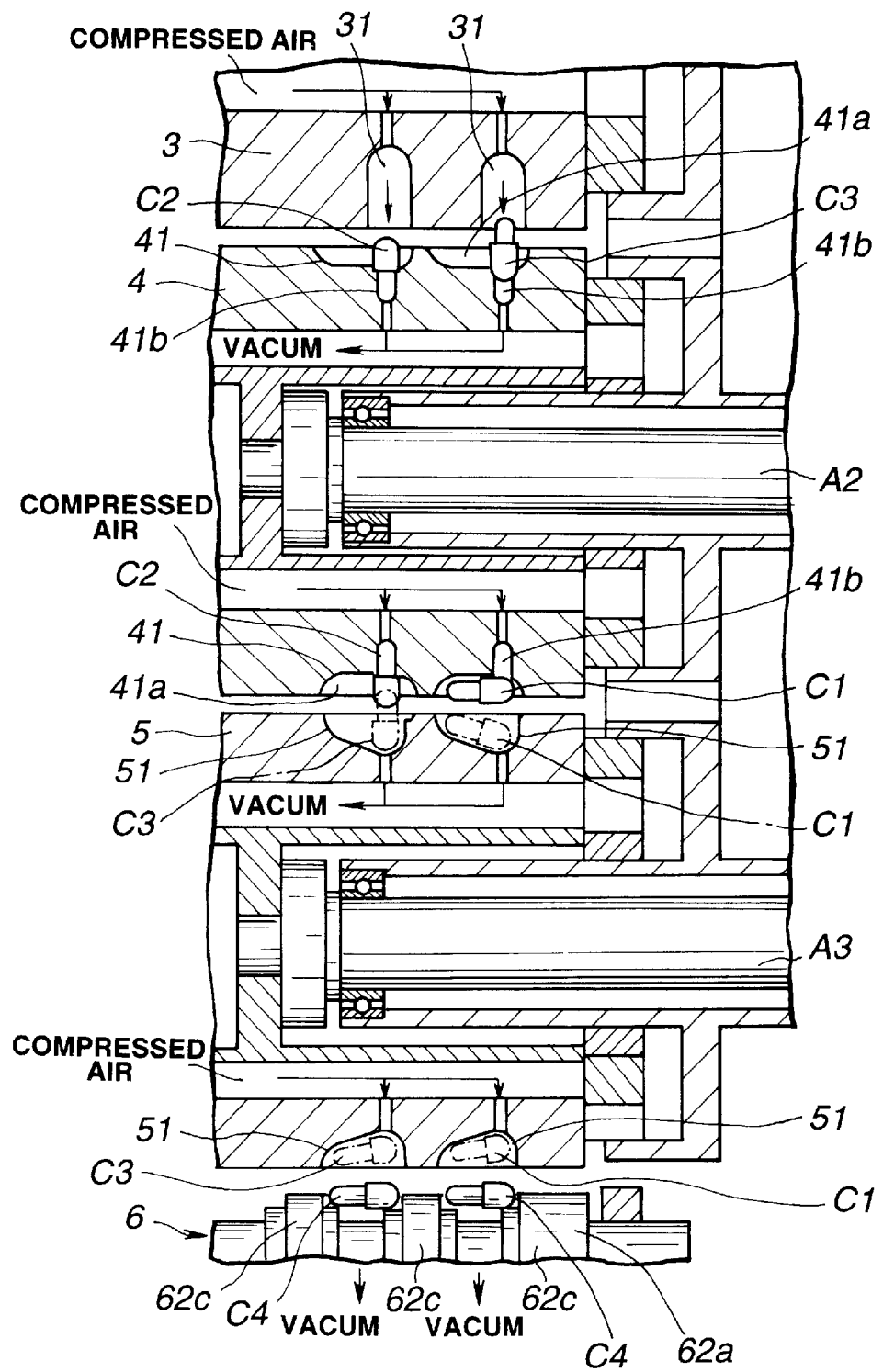
FIG. 8 is a view illustrating actions of capsules in the appearance inspecting device shown in FIG. 6.
Figure 9:
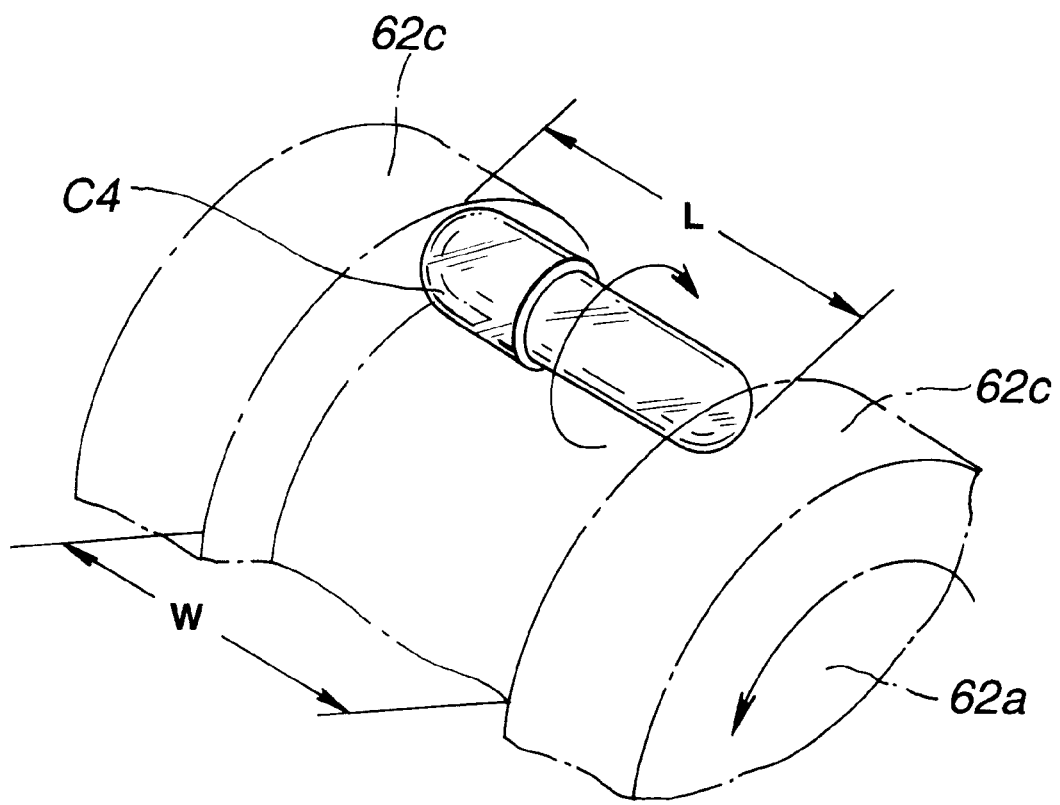
FIG. 9 is a view illustrating a state in which a capsule is held in the inspecting drum of the appearance inspecting device shown in FIG. 6.

A plurality of lead-through holding pockets 121 are formed so as to be aligned in a peripheral wall of the outer cylinder 12. As shown in FIG. 5, the lead-through holding pocket 121 is formed in an approximately oblong-shape. The length of the lead-through holding pocket 121 is formed to be longer than that of a capsule C4 to be inspected, and a center axis 121a thereof is offset a specific angle θ from an axial direction 12a of the outer cylinder 12. In addition, the angle θ between the center axis 121a of the lead-through holding pocket 121 and the axial direction 12a of the outer cylinder 12 is not particularly limited and is suitably selected depending on various conditions. In general, the angle θ is usually in a range of about 1° to 5°.

As shown in FIG. 3, the outer cylinder 12 is rotatably mounted-around the outer periphery of the inner cylinder 11. A central portion of a side wall 123 of the outer cylinder 12 is fixedly connected to an intermittently rotatable shaft 122 disposed on a center axis of the inner cylinder 11. The intermittently rotatable shaft 122 is connected to an intermittently driving device (not shown), so that the outer cylinder 12 integrated with the intermittently rotatable shaft 122 is intermittently rotated by the intermittently driving device. Thus, the lead-through holding pockets 121 formed in the peripheral wall of the outer cylinder 12 are circumferentially moved along the outer peripheral surface of the inner cylinder 11.

Reference numeral 7 in FIG. 1 indicates an image pickup device including a line sensor camera 74 and an illuminating device 75. The line sensor camera 74 photographs capsules rotated in a state being placed on the roller 13 within the lead-through holding pockets 121 of the outer cylinder 12 intermittently stopped. At this time, the capsules are illuminated by the illuminating device 75. The photographing position on the inspecting drum 1 at which the capsule is photographed by the image pickup device 7 is not particularly limited; however, it is preferably selected at a position offset about 20° to 40° on the downstream side in the carrying direction from the uppermost point of the inspecting drum 1 in consideration of stability of the capsule. Reference numeral 73 in FIG. 1 indicates a cover disposed on an upper portion of the defective capsule recovery can 71. The cover 73 allows a defective capsule blown from the lead-through holding pocket 121 by compressed air jetted from the defective capsule ejecting nozzles to be certainly recovered in the defective capsule recovery can 71. Reference numeral 14 in FIG. 1 indicates a falling preventive plate disposed along the outer periphery of the outer cylinder 12 on the downstream side from the portion at which defective capsules are ejected by the defective capsule ejecting nozzles. The falling preventive plate 14 prevents capsules from being fallen from the lead-through holding pocket 121 before being carried to the nondefective capsule recovery chute 72.

While not shown, an infrared ray sensor is mounted in the cover 73 for detecting the fact that a defective capsule is blown from the lead-through holding pocket 121 and passes through the cover 73. That is, it can be confirmed that the defective capsule is ejected from the lead-through holding pocket 121. In the case where a plurality of defective capsules are present in a row of the lead-through holding pockets 121, capsules are sequentially ejected one at a time, and the number of times the capsules passe through the infrared ray sensor are detected, to thereby detecting the fact that all of the defective capsules are ejected. If it is detected by the infrared ray sensor that the defective capsules remain in the inspecting drum 1, the inspecting device is automatically stopped to prevent the defective capsules from being mixed with nondefective capsules.

Reference numeral 9 in FIG. 1 indicates a charging hopper for charging capsules to be inspected into the appearance inspecting device. Capsules are charged from the charging hopper 9 into the supply hopper 2 in the inspecting device. Reference numeral 10 in FIG. 1 indicates an operational board for setting various inspecting conditions. The operational board 10 includes a monitor for displaying an inspection state.

According to the appearance inspecting device in this embodiment, capsules are charged from the charging hopper 9 into the inspecting device, being once contained at random in the supply hopper 2, and are aligned in upright states in the supply drum 3. All of the capsules are then direction-restricted into laterally-turned states with the cap sides being directed in a specific direction by the first and second direction restricting drums 4 and 5, and are supplied into the inspecting drum 1. Such a series of actions are the same as those performed using the above-described related art appearance inspecting device (see FIGS. 6 to 9).

Next, the capsules C4 supplied from the second direction restricting drum 5 into the inspecting drum 1 in the state being direction-restricted are contained in the lead-through holding pockets 121 of the outer cylinder 12 constituting the inspecting drum 1, and are carried by intermittent rotation of the outer cylinder 12 in such a manner as to be intermittently revolved. In the course of carrying of the capsules C4, the capsules C4 are rotated by the roller 13 being rotated on its axis in the inspecting drum 1 and are photographed by the line sensor camera 74 of the image pickup device 7. From the images of the capsules thus obtained, it is determined by the quality determining section (not shown) whether the capsules (solid formulations) are defective or nondefective in appearance, and on the basis of the determined results, defective capsules are blown from the lead-through holding pockets 121 into the defective capsule recovery can 71 by the defective capsule ejecting nozzles (not shown) and the remaining nondefective capsules are blown into the nondefective capsule recovery chute 72 by the nondefective capsule ejecting nozzles (not shown). Thus, the capsules C4 are classified into the defective capsules and the nondefective capsules which are in turn respectively recovered.

In this case, according to the appearance inspecting device in this embodiment, the inspecting drum 1 includes the fixed inner cylinder 11 and the outer cylinder 12 intermittently rotatably mounted outside the inner cylinder 11 and the capsules C4 are carried in the states being contained in the lead-through pockets 121 provided in the outer cylinder 12, and consequently, as shown in FIG. 2, the capsules C4 are carried while being rolled on the outer peripheral surface of the inner cylinder 11 in the states being held in the lead-through holding pockets 121.

When being carried up to the portion where the roller 13 being rotatable on its axis is disposed and intermittently stopped, the capsules C4 are placed on the surfaces of the projecting rings 13a of the roller 13 which surfaces are exposed from the outer peripheral surface of the inner cylinder 11, as shown in FIG. 4, and are then rotated by rotation of the roller 13 on its axis within the lead-through holding pockets 121. To be more specific, the capsules C4 are rotated so as to be rolled on the surfaces of the projecting rings 13a of the roller 13 being rotated on its axis in the states being held in the stopped lead-through holding pockets 121.

As shown in FIG. 5, the lead-through holding pocket 121 for holding the capsule C4 is formed in the state in which the center axis 121a is offset the specific angle θ from the axial direction 12a of the outer cylinder 12, and accordingly, the center axis 121a of the lead-through holding pocket 121 is also offset the specific angle from the rotational shaft A5 of the roller 13 disposed along the axial direction of the inner cylinder 11. As a result, the rotational shaft of the capsule C4 rolled on the surface of the projecting ring 13a of the roller 13 while being held in the lead-through holding pocket 121 is offset from the rotational shaft A5 of the roller 13. Thus, the capsule C4 is rolled on the surface of the projecting ring 13a of the roller 13 in the direction offset obliquely from the rotational direction of the roller 13 in the state being held in the lead-through holding pocket 121. Consequently, each capsule C4 in the lead-through holding pocket 121 is shifted to one end side (right side in FIG. 5) of the pocket 121. Further, the projecting ring 13a of the roller 13 is, as described above, formed in such a shape that the surface thereof is downward tilted in cross-section toward one axial end side, so that the capsule C4 rotated on the tilted surface of the projecting ring 13a tends to be moved toward the one axial end side (right side in FIG. 5). That is, the capsule C4 is rotated on the projecting ring 13a of the roller 13 while certainly keeping the state in which the capsule C4 is shifted to the one end side (right side in FIG. 5) of the lead-through holding pocket 121. In this embodiment, as shown in FIG. 5, the capsule C4 is shifted on the cap side (on the right side) in the figure.

Further, in the appearance inspecting device in this embodiment, when the capsule C4 is started to be rotated on the projecting ring 13a of the roller 13 being rotated on its axis, the capsule C4 is certainly shifted to the one end side (cap side) by suction through the gap 13a provided between the projecting ring 13 and the roller insertion window 11a of the inner cylinder 11. Such a suction state is certainly kept during rotation of the capsule C4. Additionally, since the peripheral surface of the capsule C4 on the cap side is abutted against the rubber member 13b mounted at the downward tilted edge portion of the projecting ring 13a, the rotation of the capsule C4 can be certainly stably performed by the frictional resistance of the rubber member 13b.

Since the center axis 121a of the lead-through holding pocket 121 is offset the specific angle θ from the axial direction 12a of the outer cylinder 12, the capsule C4 carried by rotation of the outer cylinder 12 while being held in the lead-through holding pocket 121 and rolled on the outer peripheral surface of the inner cylinder 11 is rolled in the direction offset from the rotational direction of the outer cylinder 12, so that the capsule C4 can be shifted on one end side of the lead-through holding pocket 121 during a period for which the capsule C4 is carried to the portion where the roller 13 is disposed. In this case, by setting the end portion to which the capsule C4 is shifted during carrying to be identical to the end portion to which the capsule C4 is shifted during rotation on the projecting ring 13a of the roller 13, the capsule C4 shifted on the one end side (cap side) of the lead-through holding pocket 121 during carrying is allowed to be rotated on the projecting ring 13a of the roller 13 while keeping the state in which the capsule C4 has been shifted on the one end side (cap side) during carrying. In the inspecting device of this embodiment, however, since the capsule C4 can be, as described above, certainly moved (shifted) to the one end side (cap side) of the lead-through holding pocket 121 while being rotated on the projecting ring 13a of the roller 13, the direction in which the capsule C4 is shifted during carrying may be set to be reversed to the direction in which the capsule C4 is shifted on the projecting ring 13a of the roller 13.

In this way, according to the appearance inspecting device in this embodiment, all of the capsules C4 held by the inspecting drum 1 can be positioned to be shifted to one end sides of the lead-through holding pockets 121, and the capsules C4 which are rotated while certainly keeping the positioned states can be photographed. Accordingly, it is possible to certainly obtain clear images of the capsules without occurrence of disturbance such as deviation, and hence to inspect appearances of the capsules at high accuracies under a strictly determined quality criterion.

In this case, according to the appearance inspecting device in this embodiment, capsules each having a cap and a body are direction-restricted in laterally-turned states with the caps being directed in a specific direction, being supplied to the inspecting drum 1 in these states, and are all positioned to be shifted to the cap sides in the lead-through holding pockets 121, followed by inspection of appearances of the capsules C4, so that it is possible to inspect an appearance of each capsule in a state that a stepped portion formed at a boundary between the cap and the body is accurately positioned. Thus, it is possible to detect a failure such as a fine split-like damage or crack liable to produced in the vicinity of the stepped portion of each capsule while certainly identifying it from the stepped portion in accordance with the related art method in which a change in image data due to the stepped portion is previously stored, and hence to easily attain a strict appearance inspection for capsules.

To be more specific, for a capsule in which a cap and a body are connected to each other, a connection length between the cap and the body is slightly varied, and thereby the entire length of the capsule is not necessarily specified; however, since the length of the cap fitted around the body is usually specified. Accordingly, in this embodiment, a boundary between the cap and the body can be accurately positioned by shifting the capsule to the cap side. Thus, a change in image data due to the above-described stepped portion can be estimated and stored, and further a position on an image on which the change in data due to the stepped portion appears can be certainly specified, so that a failure such as a damage which occurs as an abnormality different from the change previously stored can be easily detected while being certainly identified from the above stepped portion.

Further, according to the appearance inspecting device in this embodiment, as described above, since all of the capsules C4 to be inspected are photographed in the states being shifted on one end sides in the lead-through holding pockets 121, one-ends (leading ends on the cap sides) of the capsules are lined up in images thus obtained so that lengths of the capsules can be accurately inspected by detecting the other ends (leading ends on the body sides) of the capsules. As a result, the lengths of capsules can be inspected simultaneously with usual appearance inspection.

In this way, according to the appearance inspecting device in this embodiment, it is possible to attain a high inspecting accuracy being sufficiently satisfied in terms of practical use, and also to perform length inspection simultaneously with usual appearance inspection.

The appearance inspecting device of the present invention is not limited to the above-described embodiment but can be variously changed. For example, although capsules are direction-restricted in laterally-turned states with the cap sides being directed in a specific direction by provision of the supply drum 3 for supplying the capsules aligned in upright states and the two direction restricting drums 4 and 5 in the above-described embodiment, the direction restricting means provided in the supply section "s" is not limited to the direction restricting drums 4 and 5 but may be of any type insofar as it can stably supply capsules to the inspecting drum 1 while restricting directions of the capsules in laterally-turned states with the caps being directed in a specific direction. Also, in the above-described embodiment, description is made by example of inspection for appearances of capsules in each of which a hard capsule piece having a cap and a body is filled with a medicine and appearances of empty capsules in each of which a cap and a body are temporarily connected to each other before being filled with a medicine; however, a solid formulation to be inspected is not limited thereto. The inspecting device of the present invention is suitably used for appearance inspection for soft capsules or elliptic ball-like tablets. In this case, since solid formulations are not particularly required to be direction-restricted, the direction restricting means can be omitted and the supply section "s" may be simply configured to stably supply solid formulations in laterally-turned states. The configuration of each of the mechanism for classifying capsules into defective capsules and nondefective capsules and recovering the defective and nondefective capsules respectively and the image pickup device 7 can be suitably changed. And, it is to be understood that the other configurations of the appearance inspecting device in the above-described embodiment may be variously changed without departing from the scope of the present invention.

What is claimed is:

1. An appearance inspecting device for inspecting appearances of solid formulations each having a shape being rotation-symmetric around a specific axis, comprising:

a supply section for continuously supplying said solid formulations;

an inspecting drum for holding on its outer peripheral portion said solid formulations supplied from said supply section and carrying said solid formulations in such a manner as to allow said solid formulations to be intermittently revolved, and rotating said solid formulations at a specific carrying position;

an image pickup device for photographing surfaces of said solid formulations rotated by said inspecting drum;

a quality determining section for processing images of said solid formulations picked-up by said image pickup device and determining whether said solid formulations are defective or nondefective; and a classifying means for classifying said solid formulations into defective capsules and nondefective capsules on the basis of the results determined by said quality determining section and recovering said defective and nondefective capsules;

wherein said inspecting drum includes a fixed inner cylinder, and an outer cylinder rotatably mounted on an outer periphery of said inner cylinder in such a manner as to be intermittently rotated along the outer peripheral surface of said inner cylinder;

a roller rotatable on a rotational axis extending along the axial direction of said inner cylinder is provided inside a portion of said inner cylinder in a state in which a surface of said roller is exposed from the outer peripheral surface of said inner cylinder;

the surface of said roller, exposed from the outer peripheral surface of said inner cylinder, is formed into a cross-sectional shape being tiled downward to one axial end side; and said outer cylinder has lead-through holding pockets each being formed into an elliptic, oblong, or rectangular shape having a center axis offset a specific angle from the axial direction of said outer cylinder;

whereby said solid formulations are held in said lead-through holding pockets and carried by intermittent rotation of said outer cylinder; said solid formulations in said lead-through holding pockets intermittently stopped at a specific carrying position are rotated on said roller being rotated on the rotational axis; and outer peripheral surfaces of said solid formulations thus rotated are photographed by said image pickup device.

2. An appearance inspecting device according to claim 1, wherein a ring-like rubber member is circumferentially mounted at an edge portion of the surface of said roller on the downward tilted side.

3. An appearance inspecting device according to claim 1, wherein said solid formulation is a hard capsule including a cap and a body; and said supply section is provided with a direction restricting means for aligning said capsules with the cap sides being directed in a specific direction, whereby said capsules are carried while being contained in said lead-through holding pockets of said outer cylinder in states being restricted in a specific direction by said direction restricting means.

4. An appearance inspecting device according to claim 3, wherein said supply section comprises:

a supply hopper for containing a specific number of capsules once and sequentially supplying said capsules to a supply drum;

said supply drum which has a plurality of supply pockets aligned in its outer peripheral surface and is rotated around a horizontal axis, said plurality of supply pockets being adapted to contain said capsules in upright states with axial lines of said capsules being directed up and down;

a first direction restricting drum which is disposed under said supply drum in such a state that an outer peripheral surface thereof is in proximity to the outer peripheral surface of said supply drum and is rotated around a horizontal axis, and which first direction restricting drum has first direction restricting pockets aligned in the outer peripheral surface thereof at positions corresponding to those of said supply pockets, said first direction restricting pockets being adapted to perfectly contain capsules in laterally-turned states with axial lines thereof being directed in the horizontal direction and capsules in upright states with caps thereof being directed upward and also being adapted to receive capsules in upright states with bodies thereof being directed upward in such a state that the body portions project from the outer peripheral surface of said first direction restricting drum;

a first direction restricting guide which is provided along the outer peripheral surface of said first direction restricting drum and has a pushing portion slightly tilted from the rotational direction of said first direction restricting drum, said pushing portion being adapted to laterally push end portions of said capsules on the body sides projecting from the outer peripheral surface of said first direction restricting drum and hence to laterally turn said capsules in said first direction restricting pockets;

a second direction restricting drum which is disposed under said first direction restricting drum in such a state that an outer peripheral surface thereof is in proximity to the outer peripheral surface of said first direction restricting drum and is rotated around a horizontal axis, and which second direction restricting drum has second direction restricting pockets aligned in the outer peripheral surface thereof at positions corresponding to those of said first direction restricting pockets, said second direction restricting pockets being adapted to perfectly contain capsules in laterally-turned states and also being adapted to receive capsules in upright states in such a state that one-end portions of said capsules project from the outer peripheral surface of said second direction restricting drum; and a second direction restricting guide which is provided along the outer peripheral surface of said second direction restricting drum and has a pushing portion slightly tilted from the rotational direction of said second direction restricting drum, said pushing portion being adapted to laterally push end portions of said capsules on the body sides projecting from the outer peripheral surface of said second direction restricting drum and hence to laterally turn said capsules in said second direction restricting pockets.

* * * * *